United States Patent [19]
Gaskill

[11] Patent Number: 5,827,212
[45] Date of Patent: Oct. 27, 1998

[54] SPLINTING DEVICE FOR AURICULAR HEMATOMA

[76] Inventor: J. Richard Gaskill, 55 Church St., #1202, Los Gatos, Calif. 95030

[21] Appl. No.: 955,775

[22] Filed: Oct. 22, 1997

[51] Int. Cl.$^6$ .............................. A63F 13/00; A63F 11/00; A63F 13/12
[52] U.S. Cl. ................................ 602/53; 128/864; 602/74
[58] Field of Search ................................ 602/5, 6, 53, 74; 128/857, 864, 866; 2/423

[56] References Cited

U.S. PATENT DOCUMENTS

| | | | |
|---|---|---|---|
| 2,958,325 | 11/1960 | Claydon et al. | 602/6 |
| 3,169,523 | 2/1965 | French | 128/864 |
| 4,844,094 | 7/1989 | Grim | 602/27 |
| 5,295,950 | 3/1994 | Godley . | |
| 5,718,244 | 2/1998 | Thornton | 128/864 |

OTHER PUBLICATIONS

Dimeff, Robert J., and Hough, David O.; "Preventing Cauliflower Ear With a Modified Tie–Through Technique," The Physician and Sports Medicine, vol. 17, No. 3, Mar. 1989, pp. 169–173.

Otolaryngology—Head and Neck Surgery, 2nd Ed., vol. 4, Chap. 159, 1993 (Mosby Year Book), pp. 2865–2866.

*Primary Examiner*—Richard J. Apley
*Assistant Examiner*—Denise Pothier
*Attorney, Agent, or Firm*—Mark E. Baze; Larry B. Guernsey

[57] ABSTRACT

An improved ear pressure dressing or splinting device 10 of the suture compression type is provided for treatment and prevention of recurrence of auricular hematoma. The splinting device 10 includes a pair of first and second backing members (12 and 14), a pair of first and second pressure pads (16 and 18), and a fastening assembly 20. The backing members (12 and 14) and pressure pads (16 and 18) are assembled in pairs in opposing, facing relation to compressibly engage the injured portion of an ear 22. The fastening assembly 20 includes a wire element 56 and a pair of first and second holdfasts (58 and 60). The wire element 56 is passed through the injured portion of the ear 22 and through apertures (36 and 38, 52 and 54) present in the backing members (12 and 14) and pressure pads (16 and 18). Proper pressure is achieved by tensioning of the fastening assembly 20 using the holdfasts (56 and 60), which are clampable upon the wire element 56, and by virtue of the nature of the material from which the backing members (12 and 14) are made. The material utilized for the backing members (12 and 14) is sufficiently malleable by hand so that a tailored shape may be obtained to conform to the convolutions of the ear 22. The material also has a good torsional rigidity to exert a uniformly distributed pressure over the entire surface of the injured portion. Such a preferred material is lead sheeting.

3 Claims, 4 Drawing Sheets

SPLINTING DEVICE FOR AURICULAR HEMATOMA

TECHNICAL FIELD

The present invention relates generally to surgical or wound pressure dressings and the like, and more particularly to an improved suture compression dressing for use in treatment of auricular hematoma.

BACKGROUND ART

The prominent position of the ear makes it prone to injuries, especially when contact sports such as boxing, wrestling, and judo are engaged in and if protective headgear is not worn. Blunt or shearing traumas to the external ear can result in auricular hematoma, which occurs when blood and serum accumulate in the subperichondral spaces of the external ear. If left untreated, or more commonly, if treated improperly, the hematomas become fibrotic, resulting in a disfiguring condition known as "cauliflower ear," "scrum ear," or "boxer's ear" or "wrestler's ear."

Treatment of auricular hematoma typically involves needle aspiration of the hematoma or, better, incision and drainage, followed by compression of the injured area to prevent re-accumulation of fluid. The application of pressure is crucial to prevent deformity.

Many different compression techniques using pressure dressings have been employed to keep the skin in the necessary close contact with the cartilage during healing. The pressure dressings generally fall into the categories of suture compression dressings, mastoid dressings (i.e., dressings attached to the head by gauze or adhesive tape), and molds (e.g., silicone) which are used with or without suturing or mastoid dressings. A number of these techniques are described in an article entitled "Preventing Cauliflower Ear With A Modified Tie-Through Technique," *The Physician and Sports Medicine*, Vol. 17, No. 3, March 1989, pp. 169—173, by Robert J. Dimeff, M. D. and David 0. Hough, M. D.

Mastoid dressings are generally disfavored because of their bulkiness and tendency to come loose or be dislodged. Suture dressings, while invasive, are less bulky and more often effective. Molds generally tend to be expensive and time consuming to apply. Since molds are very closely conforming, they do, however, tend to apply a more uniform pressure with force vectors that are directed orthogonally to a greater area of the structure involved in the injury.

A favored suture compression dressing has been a "tie-over" or "tie-through" pressure dressing using cotton balls or dental rolls, or a similar dressing material, in which these materials are placed (with an antibiotic) on opposing sides of the injured portion of the ear and are held firmly in place with a number of sutures which are passed through the cartilage of the ear and over and around the dressing materials. The dressing is then worn for several days until re-accumulation of blood is not a concern. This well-known technique is shown in the book *Otolaryngology—Head and Neck Surgery* 2nd Ed., Vol. 4, Chap. 159, at pages 2865–2866.

The tie-through technique just described is sometimes unable to provide an evenly distributed pressure over the injured area. As a result, the hematoma may reform, whereupon the blood must again be aspirated or drained, increasing the likelihood of both infection and deformity. Additionally, the procedure generally requires a number of through-and-through sutures, which can be painful, and which again increase the chance for infection.

In the modified tie-through technique recommended by Drs. Dimeff and Hough, two buttons—which are substantially identical to ordinary clothes buttons—are sewn loosely to opposing sides of the ear via two punctures through the ear (the punctures correspond to the two apertures present in each button). Before tightly securing the buttons, a contoured packing is placed under the anterior button, and the device is worn for several days as before.

The button "splint" method is simpler than suturing directly over and around the packing material and is somewhat more likely to achieve a uniform pressure while at the same time requiring a smaller number of suture penetrations. However, because the rigid buttons do not have an ability to conform to the various convolutions that comprise the topography of the ear (and it should be noted that the cartilaginous aspects of human ears vary considerably from individual to individual), the compression forces are not always exerted as closely perpendicularly to certain portions of the injured area as is what is desirable to maintain a consistent skin to cartilage contact. Additionally, the area encompassed by the injury will often be such that direct pressure by the buttons cannot be applied to the farther extents of the injury, which must rely on the leveraged—and necessarily different—pressure afforded by packing material that extends beyond the perimeter of the anterior button.

Shown in U.S. Pat. No. 5,295,950, issued to Godley in 1994, is an ear pressure dressing which attempts to avoid the limitations of both the suture- and mastoid-type dressings. Godley provides a thin piece of metal upon which are adhered a pair of pads. The metal is sufficiently ductile to be folded over the helix of the ear (the peripheral cartilaginous rim portion), whereupon the pads are caused to engage opposing sides of the injured portion of the ear and exert pressure thereon in a splinting fashion.

Use of the invention of Godley is believed to be problematic in several respects. For one, the amount of pressure that can be leveraged for application to points distant from the helix is limited, and there will naturally be an uneven gradient of pressure from the attachment site at the helix to points inward. In addition, while it is claimed that the invention is conformable to the particular shape of a patient's ear, it seems clear that this is a reference to the shapeability of the device for attachment to the helix, since more extensive conformation to the actual convolutions of the ear (e.g., the antihelix or triangular fossa, which may be quite prominent in some individuals) would seemingly result in an unworkable distortion of the device.

Because of the limitations associated with present ear pressure dressings, a great need still exists for such a dressing that is capable of applying a uniform pressure, with compression forces that are generally perpendicular to all of the relevant surfaces of the injured portion, and which is minimally invasive, simple and expeditious to apply, and inexpensive.

DISCLOSURE OF THE INVENTION

Accordingly, it is an object of the present invention to provide an improved suture compression dressing or splinting device for the treatment of auricular hematoma.

It is another object of the invention to provide such a splinting device which utilizes backing members (splints) made from a material which is malleable to be conformable to the major topography of the injured portion of a particular ear, yet rigid enough to exert sufficient pressure at points distant to the site of attachment of the device upon the ear.

It is a further object to provide such a splinting device in which a minimum number of suture penetrations through the ear are required.

It is yet another object to provide such a splinting device in which the tensioning suture wire may easily and quickly secured with clampable retaining elements.

It is yet a further object to provide such a splinting device which may be easily sized and shaped to fit any ear.

It is still another object of the present invention to provide such a splinting device which is minimally complex in construction and easily made from readily obtainable materials.

Briefly, the preferred embodiment of the present invention is an ear pressure dressing or splinting device of the suture compression type for treatment and prevention of recurrence of auricular hematoma The splinting device generally includes a pair of first and second backing members, a pair of first and second pressure pads, and a fastening assembly. The pressure pads are preferably affixed to the backing members with a self-adhesive. Each of the backing members and pressure pads includes a generally centrally located aperture. The backing members and pressure pads are assembled in pairs in opposing, facing relation, with the apertures in substantial axial alignment, to compressibly engage the injured portion of the ear. Proper pressure is achieved by tensioning of the fastening assembly and by virtue of the nature of the material from which the backing members are made.

The backing members are made from a material which is sufficiently malleable or moldable by hand so that a tailored shape may be obtained to conform to the convolutions of the injured portion of any ear. The material also has a good torsional rigidity in order that the backing members may exert a uniformly distributed pressure over the entire surface of the injured portion despite the attachment of the splinting device at only a single location on the ear. Such a presently preferred material is lead sheeting, which is easily cut and formed by hand.

The fastening assembly includes a wire element and a pair of first and second holdfasts. The wire element is passed through the injured portion of the ear and through the apertures of the backing members and pressure pads. The holdfasts are clampable upon the two ends of the wire element to tension the same. In the preferred embodiment, the holdfasts are lead "split shot"—the same type used for fishing.

An advantage of the present invention is that it is easily tailored by the physician to conform to the size and topographical features of the injured portion of the ear of any given patient.

Another advantage of the invention is that it is able to exert a substantially uniformly distributed pressure over the entire surface of the injured portion, reducing the chance for recurrence of hematoma.

A further advantage is that the force vectors that are exerted by the applied device are directed in an orthogonal relation over substantially all of the injured surface to give a proper skin to cartilage contact, to prevent "pockets" where fluid may accumulate, and to promote proper healing.

Yet another advantage is that, in most instances, attachment of the device requires but a single through piercing of the ear, reducing the chance for infection and discomfort to the patient.

Yet a further advantage is that the materials utilized in the device are readily available and inexpensive.

These and other objects and advantages of the present invention will become clear to those skilled in the art in view of the description of the best presently known mode of carrying out the invention as described herein and as illustrated in the several figures of the drawings.

DESCRIPTION AND BEST MODE OF THE INVENTION

Figure 1:
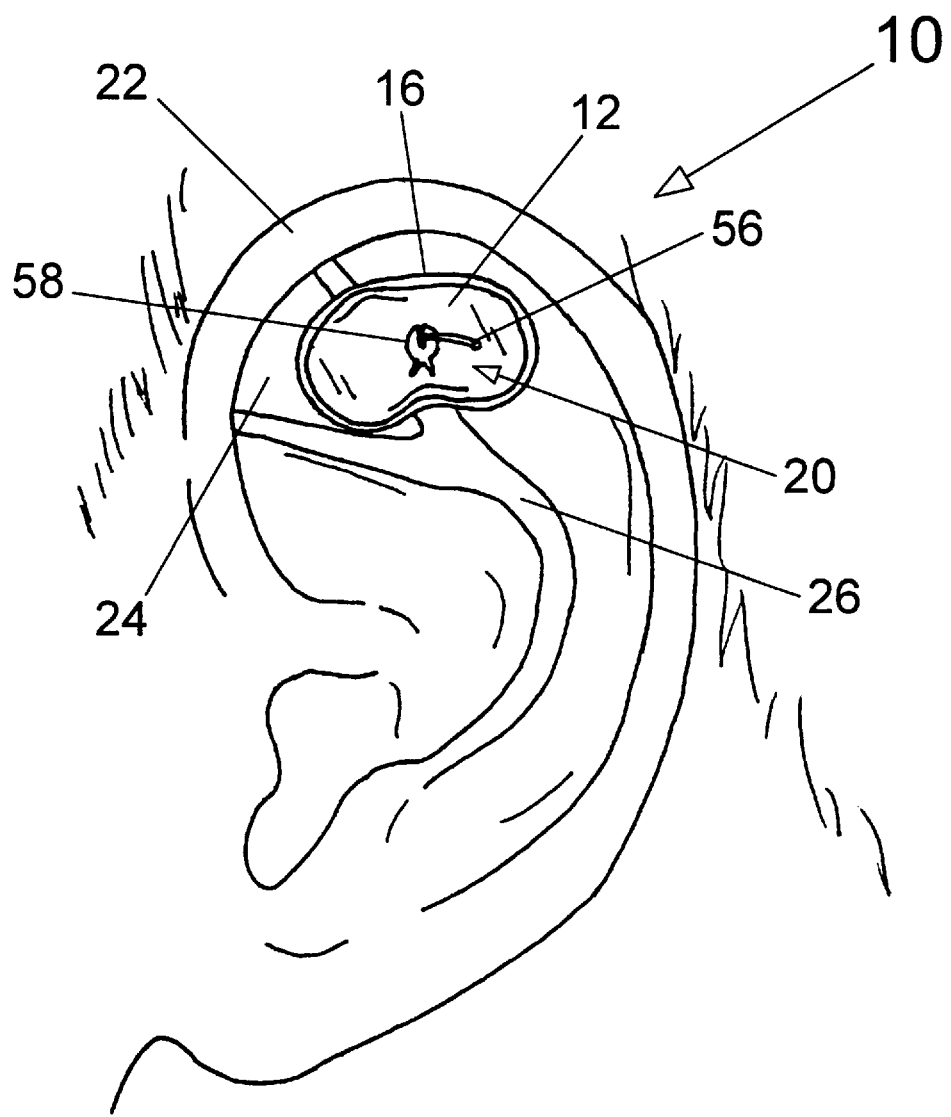
FIG. 1 is a side elevational view of a left ear with the preferred embodiment of the present invention attached in the region of the triangular fossa.

The preferred embodiment of the present invention is an ear pressure dressing or splinting device for treatment and prevention of recurrence of auricular hematoma. The splinting device of the preferred embodiment is set forth in FIGS. 1, 2, and 3, where it is designated therein by the general reference character 10.

Figure 2:
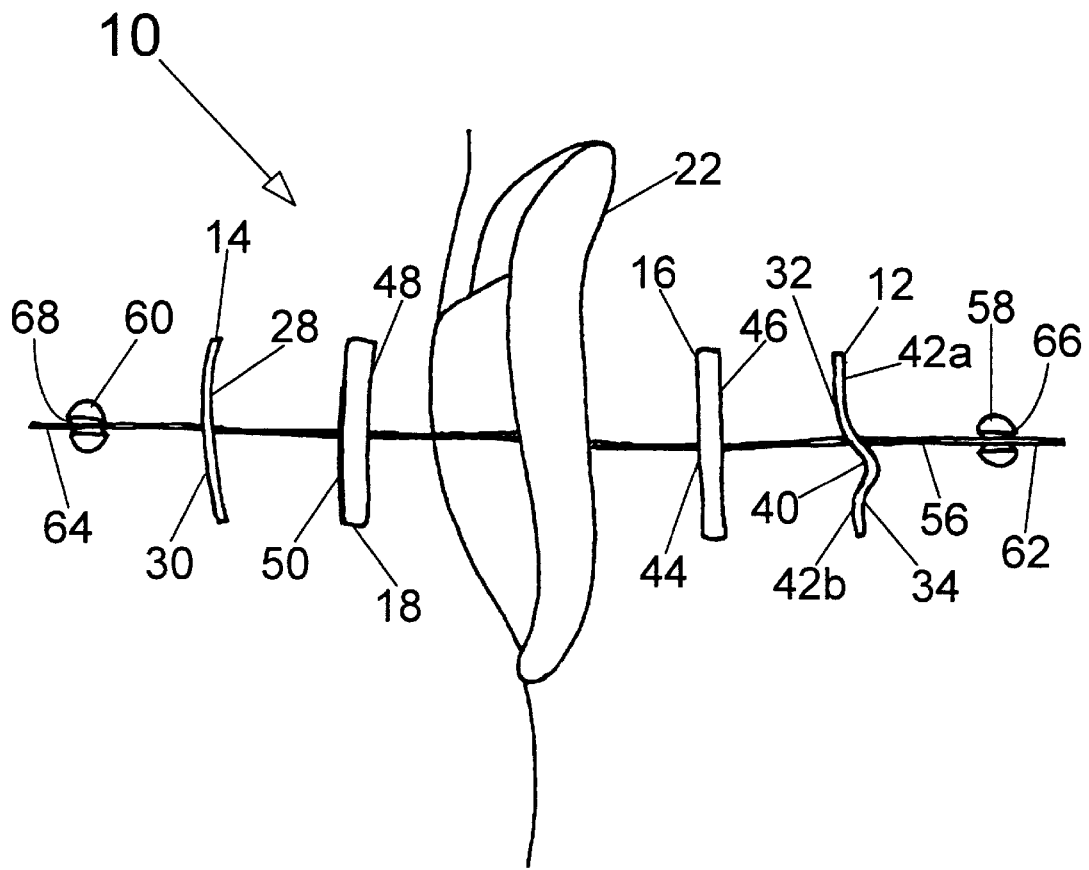
FIG. 2 is a top view of an ear with the embodiment of the invention of FIG. 1 shown in exploded fashion.
Figure 3:
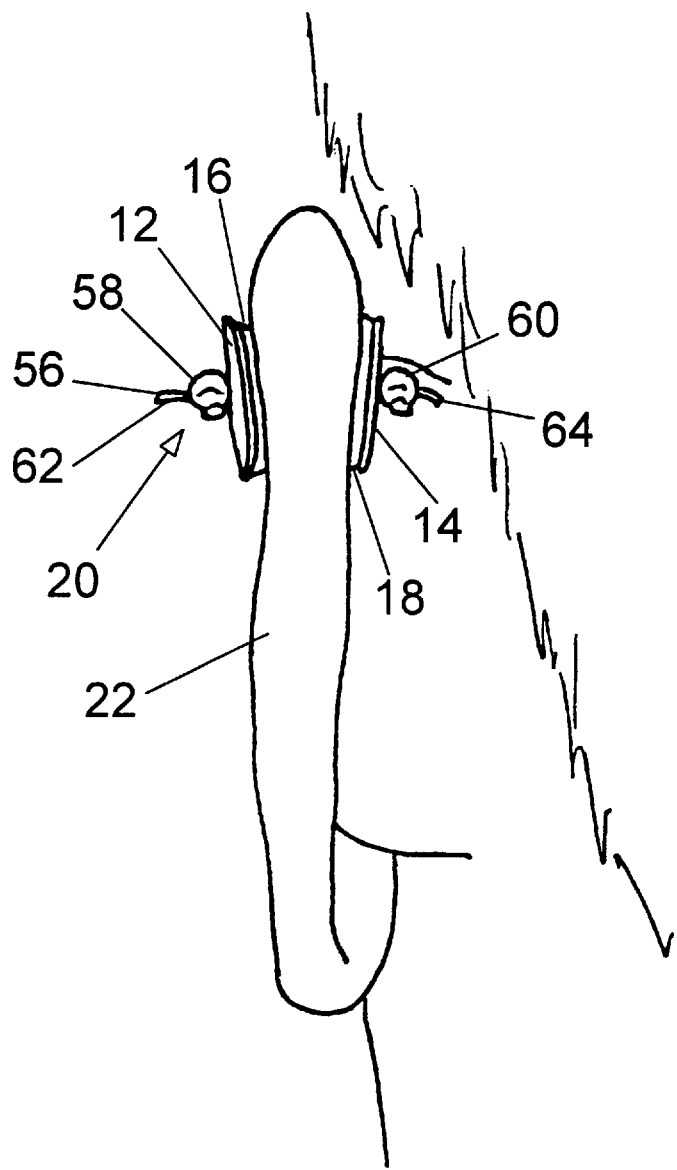
FIG. 3 is a rear view of an ear with the embodiment of the invention of FIG. 1 attached.

Referring initially to the side, top, and rear views in FIGS. 1, 2, and 3 of the drawings, respectively, the splinting device 10 is shown to be generally formed of a pair of first and second "splints" or backing members 12 and 14, respectively, a pair of first and second pressure pads 16 and 18, respectively, and a fastening assembly 20. In use, the backing members (12 and 14), and pads (16 and 18), are assembled in pairs in opposing, facing relation to compressibly engage or splint the injured portion of the ear therebetween. Proper pressure of the backing members (12 and 14) and pads (16 and 18) on the injured portion is achieved by tensioning of the fastening assembly 20 and, moreover, by virtue of the unique material structure of the backing members (12 and 14), as described in more detail below.

The splinting device 10 is shown in use with a pinna (auricle) or external ear 22 which has suffered trauma sufficient to cause a hematoma on the anterior side of the ear 22. In this instance, the area of injury is suggested to be proximate to a triangular fossa 24 or depression in the superior portion of an antihelix 26, the hematoma having been aspirated just prior to the shown use of the device 10. (In accordance with prevailing medical terminology, and in addition to the fossa 24 and antihelix 26, the external ear 22 is also shown to comprise the usual features of a helix, tragus, antitragus, and lobule.)

With reference now to FIG. 2, each of the first and second backing members (12 and 14) includes a first and second face 28 and 30, or 32 and 34, and a small diameter aperture 36 or 38 (see FIG. 4), respectively. What are denoted as the two first faces (28 and 32) are in immediate contact with the respective pressure pads (16 and 18) and are not visible during application of the splinting device 10, while the two second faces (30 and 34) are engaged by the fastening assembly 20 and are visible externally. The apertures (36 or 38) allow for attachment of the fastening assembly 20, as will be described below.

Critically, the backing members (12 or 14) each have a three-dimensional shape that has been tailored to conform to the size and topographical features of the injured portion of the external ear 22 of a particular patient. Thus, each backing member (12 or 14) will generally be of a non-standard, "cut-to-fit" size, and the shape, at least from a three-dimensional perspective, will generally be irregular and exhibit some degree of curvature (after forming). In the drawings, the backing members (12 and 14) are shown to have been formed from a generally elliptical piece of material (the important nature of which is described immediately following), but it would be apparent that any number of other geometries (e.g., circular, kidney-shaped, rounded-crescent-shaped, rounded-trapezoidal, etc.) might be created and employed depending on the location and extent of the injury.

Most critically, the backing members (12 and 14) are made from a material that is simultaneously both deformable and relatively rigid. Specifically, a material is employed which is sufficiently malleable or moldable by hand so that a shape may be obtained which fairly closely conforms to the convolutions (e.g., the antihelix 26) of the injured portion of the ear 22. And, further, the material will also have the property of exhibiting a good torsional rigidity in order that the backing members (12 and 14) may exert a uniformly distributed pressure over the entire surface of the injured portion despite the splinting device 10 having been secured to but a single point of the ear 22 and via but single points of attachment, viz. the apertures (36 and 38).

In the example shown, and especially as seen in FIG. 2, the material utilized to form the first and second backing members (12 and 14) has been arcuately bent and splayed as necessary to conform to the injured area of the fossa 24 of the antihelix 26 and the posterior area of the ear 22, respectively. Thus, an arcuate portion 40 of the first backing member 12 conformably straddles the ridge of the indicated portion of the antihelix 26, while splayed portions 42a and 42b rest on the more generally planar surrounding areas. Similarly, the second backing member 14 has been arcuately contoured to correspond to the opposing portion at the posterior of the ear 22. The backing members (12 and 14) could, of course, have an essentially infinite number of more (or less) complex configurations depending on the structures of the ear 22 involved at the injury site.

The combination of a relatively rigid material with a shape that has been conformed to the local topography provides that the force vectors that are exerted by the applied splinting device 10 are directed in a substantially orthogonal relation to the skin, perichondrium, and underlying cartilage over a substantial portion of the area of the injury. This relation is believed to be preferred since it means that further shearing or sliding of the perichondrium relative to the cartilage, at least in a localized fashion, will be less likely to occur during the compression of the injured portion, and that proper contact between the perichondrium and cartilage will be maintained to prevent further pooling of blood and serum in the subcutaneous spaces therebetween.

Presently, the most preferred material for the backing members (12 and 14) is lead sheeting in a thickness of 1.0 mm (0.04 inches). Such lead sheeting is commonly available in hospital engineering departments and may also be obtained from roofing supply outlets. This material is easily cut to any size desired using ordinary scissors. It is also easily formed to the desired shape using one's fingers. The aforementioned apertures (36 and 38) may be easily made by piercing the lead sheet with a syringe needle of medium gauge.

It would be apparent that other ductile metals in an appropriate thickness, for example, various of the aluminum alloys, might also be employed. The backing members (12 and 14) may also be made from a suitable thermoplastic material. Such a plastic can be cut and then heated as necessary to allow molding of the desired shape.

Figure 4:
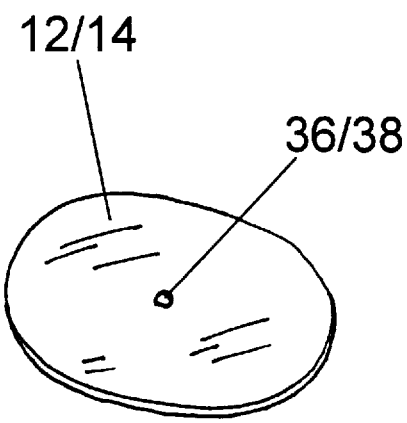
FIG. 4 is a perspective view of either of the first or second backing members prior to forming.

Referring particularly now to FIG. 4, the previously mentioned apertures (36 and 38) are, in the example shown, but single bore holes in open communication with the first and second faces (28 and 30, or 32 and 34, respectively). In other embodiments, more than one aperture (36 or 38) might be located within each backing member (12 and 14) depending on the size of the area encompassed by the injury. However, it is to be understood that it is a particular advantage of the present splinting device 10 that in many, if not most instances, only one aperture (36 or 38), and correspondingly only one piercing of the ear 22 (described below), will generally be required. As already indicated, this is because the aforementioned rigidity of the backing members (12 and 14) provides that sufficient leveraged (and uniform) force is exerted by those backing members (12 and 14) even at points relatively radially distant to the apertures (36 or 38), i.e., the marginal portions of the injured area.

Figure 5:
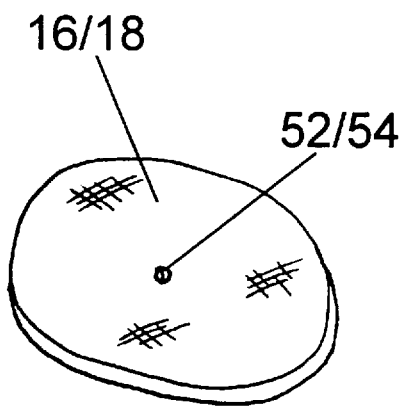
FIG. 5 is a perspective view of either of the first or second pressure pads prior to adherence to a corresponding backing member.

Referring again to FIG. 2, and also now to FIG. 5, analogously to the first and second backing members (12 and 14), each of the first and second pressure pads (16 and 18) includes a first and second side 44 and 46, or 48 and 50, and a small diameter aperture 52 or 54, respectively. The pressure pads (16 and 18) provide comfort and also allow a more uniform compression with respect to subtle topographical features of the injury site which cannot be adequately accommodated for by the necessarily rigid backing members (12 and 14).

The pressure pads (16 and 18) are cut and trimmed from a soft, compressed synthetic foam or natural sponge material, or the like, to correspond to the approximate perimeter shape of the backing members (12 and 14). The flexible nature of the pressure pads (16 and 18) permits the pads to conform to the three-dimensional shape of the formed backing members (12 and 14) and, correspondingly, to conform to the convolutions of the injured portion of the ear 22.

An adhesive material is used to affix the second sides (46 or 50) to the backing member first faces (28 or 32) so that the pressure pads (16 and 18) will maintain a correct orientation during fitting and wearing of the splinting device 10 and to facilitate assembly of the device 10. The pads (16 and 18) might be applied to the backing members (12 and 14) either before or after shaping of the backing members (12 and 14).

The presently preferred material for the pressure pads (16 and 18) is "molefoam," which is a latex pad with a soft fabric or cloth on what is denoted as the first side (42 or 46) and an adhesive layer on the second side (44 or 48). This material is advantageously "self-adhesive," which in this context means that the material is such that two adjacent layers, namely the second sides (46 or 50) and the first faces (28 or 32), can remain adhering to one another without the use of supplementary fastening elements. That the first side 42 is a soft fabric affords additional comfort and allows for both the absorption of blood fluids and of an antibiotic ointment that is desirably applied prior to fixing the splinting device 10 on the ear 22. Molefoam is available from Schering-Plough Health Care Products, Inc., Memphis, Tenn. It would be apparent that other materials might be employed as well, albeit less effectively, including sterile cotton wadding and the like.

After the pressure pads (16 and 18) have been affixed to the backing members (12 and 14), the apertures (52 and 54)

are easily formed by burning with a hot probe using the apertures (36 and 38) already present in the backing members (12 and 14) as guides.

Referring now to FIGS. 1, 2, and 3, the fastening assembly 20 comprises a wire element 56 and a pair of first and second holdfasts 58 and 60, respectively.

The wire element 56 includes a first end portion 62 and a second end portion 64 and is of a length sufficient to extend through a thickness more than the equivalent of the thicknesses of the backing members (12 and 14), the pressure pads (16 and 18), and the injured portion of the external ear 22 combined.

The wire element 56 is preferably sterile 4-0 surgical steel suture. Such material can be commercially obtained with a cutting needle already integrally attached for simultaneous perforation of the injured portion of the ear 22 and threading of the wire component through the entry hole (similar to operation of a sewing needle and thread). The wire element 56 might also be made from a high performance plastic, e.g., a nylon polymer, or similar strong material. The steel is presently preferred as it also has an anti-infective effect.

The first and second holdfasts (58 and 60) include reversibly closable mouths 66 and 68 (see FIG. 2), respectively. The mouths (66 and 68) are used to securely clamp the holdfasts (58 and 60) onto the wire end portions (62 and 64) after the holdfasts (58 and 60) have been positioned in abutting relation to the two second faces (30 and 34) of the backing members (12 and 14) and tension exerted upon the wire element 56 to sandwichedly compress the ear 22 to the desired degree.

The holdfasts (58 and 60) are conveniently a ball structure of a small, removable lead "split shot," as commonly used for fishing. Their attachment is simple, merely requiring the squeezing together of the mouth parts. However, it will be apparent that any number of other materials and methods might be used to provide the necessary staying and tensioning of the splinting device 10. For one, and less conveniently, the first and second end portions (62 and 64) might simply be tied off with knots of sufficient size to prevent their slippage through the apertures (36 and 38). As part of a commercial kit, a suture wire might even be provided with a small ball structure (or similar enlargement) already integrally present at one end of the wire, with a cutting needle then integrally attached (as mentioned previously) at the other end.

In addition to the above mentioned examples, it is to be understood that various other modifications and alterations with regard to the types of materials used, their method of joining and attachment, and the shapes, dimensions and orientations of the components as described may be made without departing from the invention. Accordingly, the above disclosure is not to be considered as limiting and the appended claims are to interpreted as encompassing the entire spirit and scope of the invention.

INDUSTRIAL APPLICABILITY

The splinting device 10 of the present invention is designed to be an improvement in suture compression dressings for treatment of auricular hematoma and to make the treatment of the same more consistent and reliable.

Use of the splinting device 10 is simple. After having first appropriately aspirated/drained the hematoma, the extent of the area encompassed by the injury is gauged, and the first and second backing members (12 and 14) are cut, preferably from 1.0 mm (0.04 inches) lead sheeting, to be suitably sized to cover the area. As the backing members (12 and 14) are fitted for size, the backing members (12 and 14) are also bent and formed by hand to correspond to any contours of the ear encountered. In the case depicted, the first backing member 12 is bent and splayed, a little offset from center, to fit properly over a cartilaginous ridge of the antihelix 26 present in the region of the triangular fossa 24. An aperture (36 and 38) is bored or cut (using a cutting needle or other pointed object) into each backing member (12 and 14) as near to center as possible.

After the correct size for the backing members (12 and 14) has been obtained, the pressure pads (16 and 18) are cut (preferably from molefoam) to approximately the same size as corresponding ones of the backing members (12 and 14). The pressure pads (16 and 18) are then adhered to the respective backing members (12 and 14) with an adhesive, which, if molefoam has been used, simply means removing the covering paper from the self-adhesive side. Using the apertures (36 and 38) of the backing members (12 and 14) as a guide, apertures (52 and 54) are burned though the pressure pads (16 and 18) to ease introduction of the wire element 56. An antibiotic is applied to the first sides (44 and 48) of the pressure pads (16 and 18) to prevent infection.

The approximate center of the injured portion is pierced and the wire element 56 passed through. As previously mentioned, the wire element 56 is preferably sterile 4-0 surgical steel suture with a cutting needle already integrally attached for simultaneous perforation of the injured portion of the ear 22 and drawing of the wire element 56 through the entry hole.

The second backing member 14/second pressure pad 18 combination pair is threaded onto the wire element 56 at the posterior of the ear 22 and the second holdfast 60 is attached by clamping the mouth 68 upon the second end portion 46 of the wire element 56. The first backing member 12/first pressure pad 16 combination pair is likewise threaded onto the wire element 56 at the anterior of the ear 22. The wire element 56 is pulled taut on the anterior side with the second holdfast 60 made to stop and press against the second backing member 14. The first holdfast 58 is then pushed into abutment with the first backing member 12 and the mouth 66 clamped on the first end portion 62 of the wire element 56, tensioning the same. Any excess of the wire element 56 is trimmed.

The ability of the simultaneously rigid and malleable splinting device 10 to conform to the topography of the ear provides that the pressure forces are exerted orthogonally to a greater area of the injured portion of the ear as compared to previously known "button-type" splinting devices, with a pressure that is also more uniform. For the foregoing reasons, and for numerous others as have been set forth herein, it is expected that the industrial applicability and commercial utility of the present invention will be extensive and long lasting.

What is claimed is:

1. A splinting device for auricular hematoma, comprising:
 a pair of backing members, each of said backing members being relatively rigid but also sufficiently malleable to be generally conformable to a portion of the major topographical features of an external ear, each said backing member having opposing first and second faces and a generally centrally located aperture;
 a pair of soft, conformable pressure pads, each said pressure pad having first and second sides and an aperture, the second sides in engagement with the first faces of said backing members, the first sides being engageable with opposing sides of the ear, the aperture of each said pressure pad being in substantial axial alignment with the aperture of a corresponding said backing member;

a wire element passable through the apertures of said backing members and said pressure pads being adapted to pass through and surgically piece the ear;

holdfast means for securing said wire element in a tensioned manner to sandwichedly compress the ear between said backing members and;

said holdfast means includes at least one retaining element clamped upon an end of said wire element; and said retaining element is a lead, split-shot fishing weight.

2. In an improved ear dressing of the suture compression type for use in treatment of auricular hematoma, with a pair of backing members for attachment to opposing sides of an ear, each backing member including at least one generally centrally located aperture, with a soft, conforming material interposed between said backing members and the ear, and with suture means, including a wire element, for sandwichedly compressing the ear as surgically pierced between said backing members, the improvement comprising:

said backing members being made from a relatively rigid yet malleable material;

whereby the malleable nature enables said backing members to be shaped to be conformable to a portion of the major topographical features of the ear of any given patient, while the relatively rigid nature enables said backing members to exert pressure even at points relatively distant to said apertures, such that the compression of the ear occurs with force vectors directed substantially perpendicular to the topological features and with a pressure that is relatively uniform over the extent of the compressed area and, further, such that in a majority of cases, said backing members need only include one aperture requiring only one surgical piercing of the ear; the suture means further including at least one retaining element clamped upon at least one end of the wire element; and said retaining element is a lead, split-shot fishing weight.

3. A method of treating auricular hematoma, comprising the steps of:

providing a pair of relatively rigid but malleable backing members, each backing member including at least one generally centrally located aperture;

deforming one said backing member to conform to the convolutions of the anterior side of the injured portion of an ear;

deforming a second said backing member to conform to the convolutions of the posterior side of the injured portion of an ear;

providing a pair of soft, conformable pressure pads, each pressure pad including at least one generally centrally located aperture axially alignable with an aperture of a said backing member;

interposing said pressure pads between said backing members on opposing sides of the injured portion of the ear;

piercing the ear to draw a wire element therethrough, the wire element introduced through the apertures of the backing members and pressure pads; and applying holdfast means for securing the wire element in a tensioned manner to sandwichedly compress the ear between the backing members by attaching at least one clampable retaining element upon at least one end of the wire element, where said retaining element is a lead, split-short fishing weight.

* * * * *